United States Patent
Takeuchi et al.

(10) Patent No.: US 8,708,931 B2
(45) Date of Patent: Apr. 29, 2014

(54) TREATMENT TOOL FOR BIOPSY AND TISSUE COLLECTING METHOD

(71) Applicant: Olympus Medical Systems Corp., Tokyo (JP)

(72) Inventors: Saori Takeuchi, Tokyo (JP); Hideo Takachi, Yokohama (JP); Yutaka Yanuma, Tokyo (JP); Masatoshi Tonomura, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/686,339

(22) Filed: Nov. 27, 2012

(65) Prior Publication Data

US 2013/0237879 A1   Sep. 12, 2013

Related U.S. Application Data

(63) Continuation of application No. PCT/JP2012/057705, filed on Mar. 26, 2012.

(60) Provisional application No. 61/467,637, filed on Mar. 25, 2011.

(51) Int. Cl.
*A61B 10/02* (2006.01)
*A61B 8/08* (2006.01)
*A61B 8/12* (2006.01)
*A61B 10/04* (2006.01)
*A61B 1/05* (2006.01)

(52) U.S. Cl.
CPC .............. *A61B 8/0841* (2013.01); *A61B 8/12* (2013.01); *A61B 10/04* (2013.01); *A61B 10/0266* (2013.01); *A61B 10/0275* (2013.01); *A61B 1/05* (2013.01); *A61B 10/0283* (2013.01); *A61B 2010/045* (2013.01)

USPC .................................................... 600/567

(58) Field of Classification Search
CPC ............... A61B 10/02; A61B 10/0233; A61B 10/0266; A61B 10/0275; A61B 10/0283; A61B 10/045
USPC ................................................. 600/564–568
See application file for complete search history.

(56) References Cited

U.S. PATENT DOCUMENTS 4,246,902 A   1/1981 Martinez
(Continued)

FOREIGN PATENT DOCUMENTS

JP   10-248793 A   9/1998
(Continued)

OTHER PUBLICATIONS

International Search Report PCT/JP2012/057705 dated Jun. 26, 2012, together with an English language translation.

(Continued)

*Primary Examiner* — Sean Dougherty
*Assistant Examiner* — Michael C Stout
(74) *Attorney, Agent, or Firm* — Scully, Scott, Murphy & Presser, P.C.

(57) ABSTRACT

This treatment tool for biopsy includes a needle tube, which having a first aperture and a second aperture. The first aperture and the second aperture communicate with the tubular space. The second aperture is provided in a side surface of the needle tube at more proximal end side than the first aperture. In a cross-section of the second aperture, a distal end circular arc portion of an end surface of the second aperture has a distal end side inclined surface that is inclined so as to be positioned gradually outwards of a radial direction of the needle tube towards the distal end side, and a proximal end circular arc portion of the end surface of the second aperture has a proximal end inclined surface that is inclined so as to be positioned gradually outwards of the radial direction of the needle tube towards the proximal end side.

6 Claims, 14 Drawing Sheets

(56) References Cited

U.S. PATENT DOCUMENTS

| | | | |
|---|---|---|---|
| 4,660,267 A * | 4/1987 | Wheeler | 29/437 |
| 4,867,157 A * | 9/1989 | McGurk-Burleson et al. | 606/170 |
| 5,394,887 A | 3/1995 | Haaga | |
| 5,401,247 A * | 3/1995 | Yoon | 604/164.12 |
| 5,425,376 A * | 6/1995 | Banys et al. | 600/566 |
| 5,449,001 A * | 9/1995 | Terwilliger | 600/567 |
| 5,733,297 A * | 3/1998 | Wang | 606/167 |
| 5,792,166 A | 8/1998 | Gordon et al. | |
| 5,836,953 A * | 11/1998 | Yoon | 606/114 |
| 5,843,111 A * | 12/1998 | Vijfvinkel | 606/171 |
| 5,928,162 A * | 7/1999 | Giurtino et al. | 600/567 |
| 6,027,514 A * | 2/2000 | Stine et al. | 606/159 |
| 6,899,685 B2 * | 5/2005 | Kermode et al. | 600/564 |
| 7,479,117 B2 * | 1/2009 | Zadow | 600/567 |
| 2003/0032895 A1 * | 2/2003 | Fisher | 600/573 |
| 2003/0236471 A1 | 12/2003 | Fisher | |
| 2005/0177117 A1 * | 8/2005 | Crocker et al. | 604/272 |
| 2005/0283069 A1 | 12/2005 | Hughes et al. | |
| 2006/0058703 A1 * | 3/2006 | Huenerbein | 600/567 |
| 2006/0161192 A1 * | 7/2006 | Young | 606/185 |
| 2007/0167736 A1 * | 7/2007 | Dietz et al. | 600/411 |
| 2009/0209923 A1 * | 8/2009 | Linderoth et al. | 604/272 |
| 2010/0030108 A1 * | 2/2010 | Anderson et al. | 600/567 |
| 2010/0076342 A1 * | 3/2010 | Miller | 600/567 |
| 2010/0168684 A1 | 7/2010 | Ryan | |
| 2010/0280409 A1 * | 11/2010 | Mark | 600/567 |
| 2010/0305470 A1 * | 12/2010 | Ireland | 600/567 |

FOREIGN PATENT DOCUMENTS

| | | |
|---|---|---|
| JP | 2004-181095 A | 7/2004 |
| JP | 2005-270664 A | 10/2005 |
| JP | 2008-500139 A | 1/2008 |
| WO | 2009/055640 A1 | 4/2009 |

OTHER PUBLICATIONS

Extended Supplementary European Search Report from corresponding European Application No. 12 765 875.5, dated Sep. 5, 2013.

* cited by examiner

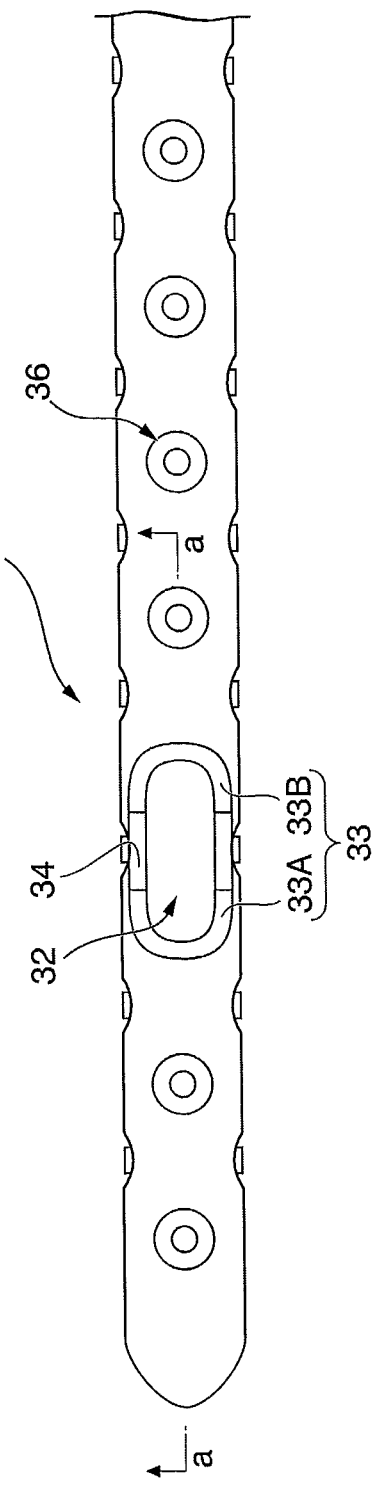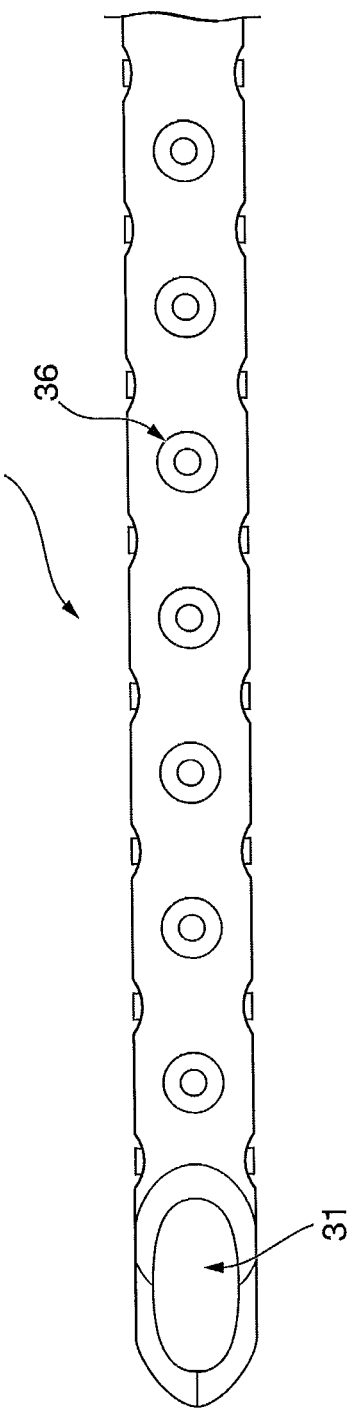
FIG. 4A
FIG. 4B

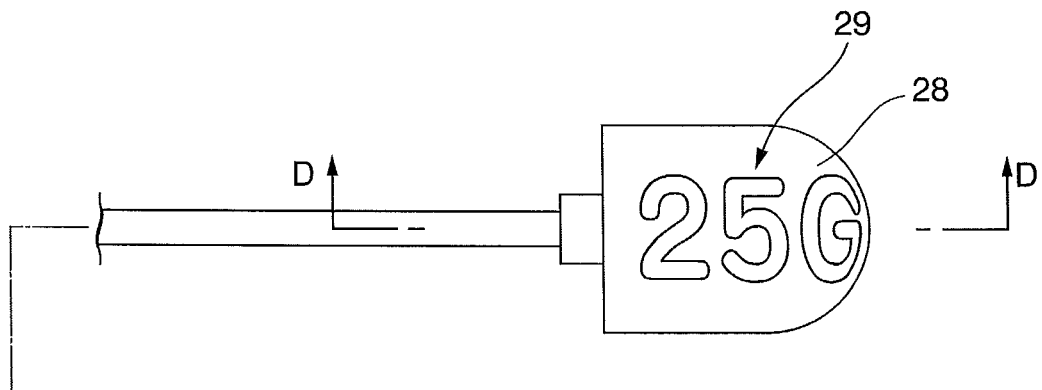
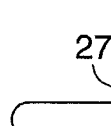
FIG. 11A
FIG. 11B
FIG. 12
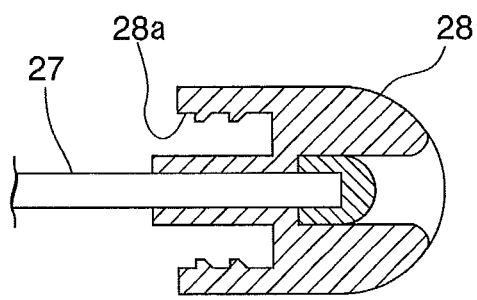

ical arc portion has a distal end
TREATMENT TOOL FOR BIOPSY AND TISSUE COLLECTING METHOD Priority is claimed on U.S. Provisional Patent Application No. 61/467,637 filed in the United States in Japanese on Mar. 25, 2011, and is a continuation application based on International Patent Application PCT/JP 2012/057705 filed on Mar. 26, 2012, and the contents of both the US Provisional patent application and the International Patent Application are incorporated herein by reference.

BACKGROUND OF THE INVENTION

1. Field of the Invention

The present invention relates to a treatment tool for biopsy that has a tubular puncture needle provided at a distal end portion thereof, and to a tissue collecting method that utilizes this treatment tool for biopsy.

2. Description of Related Art

Conventionally, the collecting of biomedical tissue from tissue within a body cavity using a tubular puncture needle (i.e., a needle tube), and then performing various types of examination on the tissue is widely known.

For example, in Japanese Unexamined Patent Application, First Publication No. H10-248793, there is disclosed a treatment tool that is provided with a needle tube having a sharp distal end that is cut diagonally relative to the axis thereof.

This type of treatment tool is made to pierce target tissue while being observed by an apparatus that is able to photograph tomographic images within a body cavity such as ultrasonic diagnostic apparatus, so that biomedical tissue is able to be collected.

SUMMARY OF THE INVENTION

According to a first aspect of the present invention, a treatment tool for biopsy includes a needle tube which is formed with a sharp distal end that is capable of piercing tissue, a tubular space a first aperture, and a second aperture. The first aperture is provided in the distal end of the needle tube and that communicates with the tubular space. The second aperture is provided, in order to collect tissue from an area punctured by the needle tube, in a side surface of the needle tube at more proximal end side than the first aperture, and communicates with the tubular space in the needle tube. When viewed from a thickness direction of the second aperture, an end surface of the second aperture has both a distal end circular arc portion and a proximal end circular arc portion that are formed in circular arc shapes respectively on the distal end side and the proximal end side in the axial direction of the needle tube, and in a cross-section taken in the thickness direction of the second aperture so as to include the axis of the needle tube, the distal end circular arc portion has a distal end inclined surface that is inclined so as to be positioned gradually outwards of the radial direction of the needle tube towards the distal end side, and the proximal end circular arc portion has a proximal end inclined surface that is inclined so as to be positioned gradually outwards of the radial direction of the needle tube towards the proximal end side.

Moreover, according to a second aspect of the present invention, in the treatment tool for biopsy according to the first aspect of the present invention, blade portions that are used to cut off tissue when the needle tube is moved backwards and forwards in the axial direction of the needle tube are formed on those end portions of the distal end inclined surface and the proximal end inclined surface that are on the second aperture side.

Moreover, according to a third aspect of the present invention, in the treatment tool for biopsy according to the first aspect of the present invention, in the cross-section taken in the depth direction of the second aperture, the distal end inclined surface and the proximal end inclined surface are formed such that portions of circular arcs of circles whose centers are predetermined points located outside the needle tube in the radial direction thereof.

Moreover, according to a fourth aspect of the present invention, in the treatment tool for biopsy according to the first aspect of the present invention, the second aperture is formed at a different phase position in comparison to the first aperture in the circumferential direction of the needle tube, and in a position where it does not overlap with the first aperture in the axial direction of the needle tube.

Moreover, according to a fifth aspect of the present invention, in the treatment tool for biopsy according to the first aspect of the present invention, the end surface of the second aperture is provided with rectilinear portions that connect gently to a proximal end portion of the distal end circular arc portion and to a distal end portion of the proximal end circular arc portion, and that extend in the axial direction of the needle tube.

BRIEF DESCRIPTION OF THE DRAWINGS

FIG. 4A is an enlarged plan view of the distal end portion of a needle tube of the treatment tool.

FIG. 4B is an enlarged bottom view of a distal end portion of the needle tube.

FIG. 11 is a side view showing a stylet of the treatment tool.

FIG. 12 is a cross-sectional view taken along a line D-D in FIG. 11A.

PREFERRED EMBODIMENTS

A treatment tool according to an embodiment of the present invention will now be described.

The treatment tool of the present embodiment is a medical instrument that is inserted into a channel of an ultrasonic endoscope such that it can be moved freely backwards and forwards, and that is used together with the ultrasonic endoscope to perform treatment within a human body.

Figure 1:
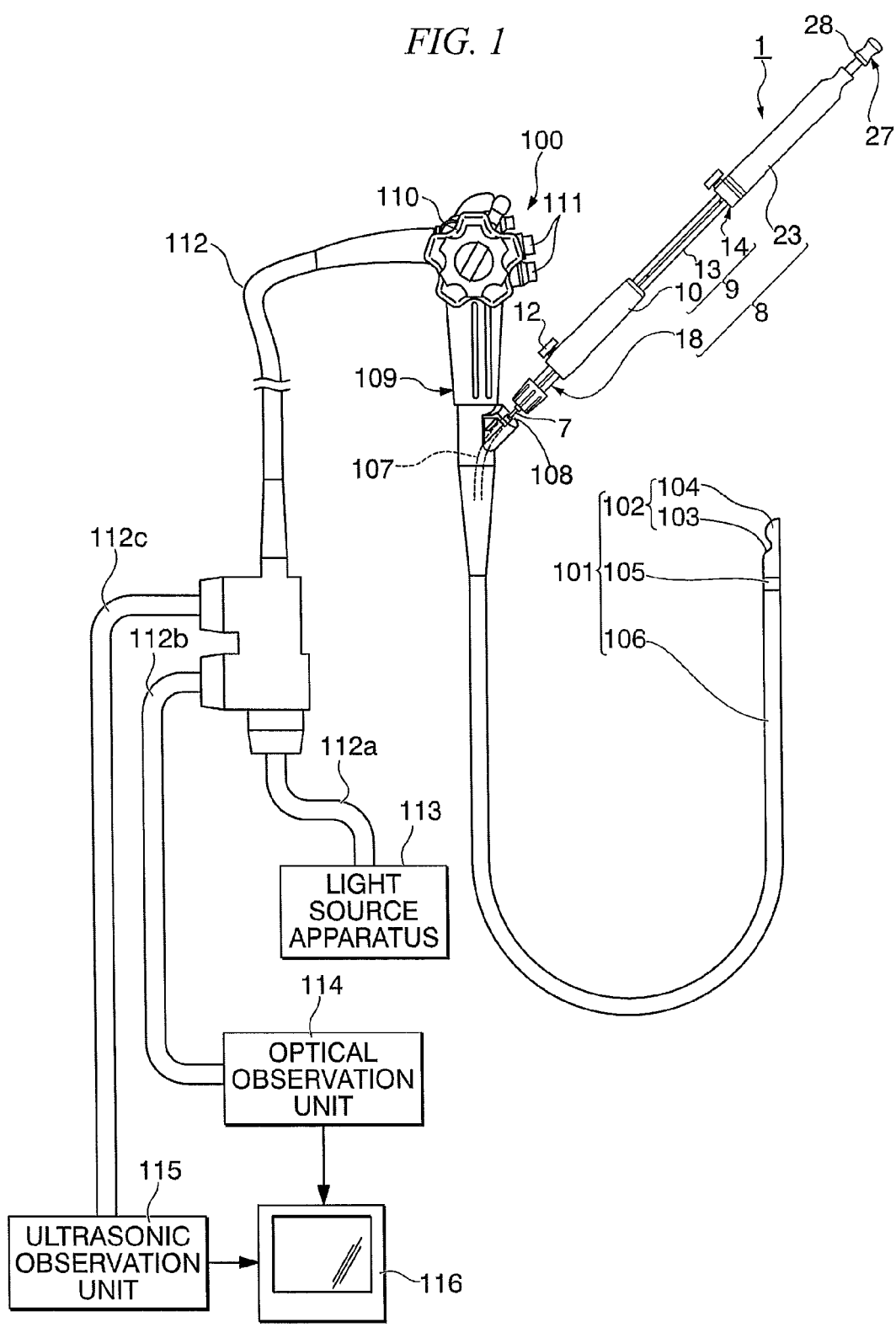
FIG. 1 is a perspective view showing the schematic structure of a treatment tool and an ultrasonic endoscope according to an embodiment of the present invention.

Firstly, the schematic structure of an ultrasonic endoscope 100 that is used together with the treatment tool 1 will be described with reference made to FIG. 1. FIG. 1 is a perspective view showing the schematic structure of a treatment tool and an ultrasonic endoscope of the present embodiment.

As is shown in FIG. 1, the ultrasonic endoscope 100 is provided with an insertion portion 101 that is inserted from its distal end into a body, an operating section 109 that is attached to a proximal end of the insertion portion 101, a universal cord 112 that one end thereof connected to a side portion of the operating section 109, a light source apparatus 113 that is connected via a branch cable 112a to the other end of the universal cord 112, an optical observation unit 114 that is connected via a branch cable 112b to the other end of the universal cord 112, and an ultrasonic observation unit 115 that is connected via a branch cable 112c to the other end of the universal cord 112.

In the insertion portion 101, a distal end rigid portion 102, a bending portion 105, and a flexible tube portion 106 are provided in this sequence from the distal end side.

The distal end rigid portion 102 is provided with an optical imaging mechanism 103 that is used to make optical observations, and an ultrasonic scanning mechanism 104 that is used to make ultrasonic observations.

The optical imaging mechanism 103 is provided with various types of structure (not shown) such as an imaging optical system whose field of view faces towards the front of the distal end rigid portion 102, an image sensor such as a CCD or CMOS that detects images of a subject that are incident via the imaging optical system, and a CCU that controls operations of the image sensor.

The ultrasonic scanning mechanism 104 is provided with an ultrasonic wave transducer that emits ultrasonic waves, and an ultrasonic wave receiver that receives ultrasonic waves (both are omitted from the drawings). The ultrasonic scanning mechanism 104 receives reflection waves that are reflected when ultrasonic waves emitted by the ultrasonic wave transducer strike against an observation subject by the ultrasonic wave receiver, and outputs signals that are based on the ultrasonic waves received by the ultrasonic wave receiver to the ultrasonic observation unit 115.

The bending portion 105 is formed in a cylindrical shape, and is able to be bent, for example, in four predetermined directions such as up-down and left-right, by pulling angle wires (not shown) that are fixed to the distal end of the bending portion 105 and extend toward the operating section 109.

The flexible tube portion 106 is a tubular component that is formed with flexibility so that it is able to guide the distal end rigid portion 102 to a desired position within the digestive tract or body cavity.

A tubular channel 107 through which the treatment tool 1 is inserted, and a conduit (not shown) that is used for supplying or suctioning air or water are provided inside each of the bending portion 105 and flexible tube portion 106.

One end of the channel 107 opens at the distal end of the distal end rigid portion 102, and the other end of the channel 107 opens at a side surface on the distal end side of the operating section 109. A proximal end connector 108 that is formed in a flange shape is fixed to the other end of the channel 107. The treatment tool 1 that is to be used together with the ultrasonic endoscope 100 can be fixed to the proximal end connector 108.

The operating section 109 has an outer surface that is formed in a shape that allows it to be held in the hand of a user who is using the ultrasonic endoscope 100, and is provided with a bending operating mechanism 110 that is used to bend the bending portion 105 by manipulating the angle wires, and with a plurality of switches 111 that are used to supply or suction air or water through the conduit.

The light source apparatus 113 is an apparatus that emits illumination light that is used by the optical imaging mechanism 103 to acquire images.

The optical observation unit 114 is constructed such that it is able to project images acquired by the image sensor of the optical imaging mechanism 103 on a monitor 116.

The ultrasonic observation unit 115 receives signals output from the ultrasonic scanning mechanism 104, and then creates images based on these signals which it then projects on the monitor 116.

Next, the structure of the treatment tool 1 of the present embodiment that is used together with the ultrasonic endoscope 100 will be described with reference made to FIG. 2 through FIG. 12.

Figure 2:
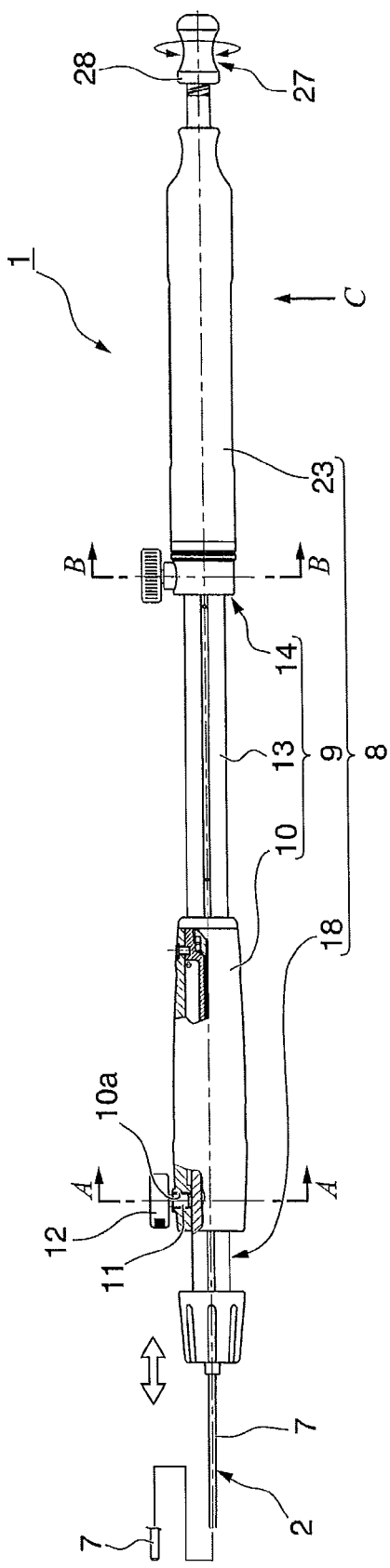
FIG. 2 is a side view showing the treatment tool in partial cross-section.
Figure 3:
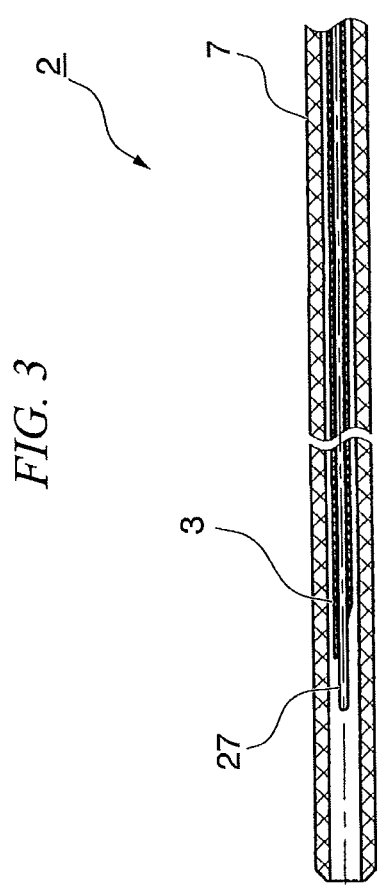
FIG. 3 is a cross-sectional view showing the structure of a distal end side of an insertion body of the treatment tool.

FIG. 2 is a side view showing the treatment tool 1 in partial cross-section. FIG. 3 is a view showing the structure of a distal end side of an insertion body 2, and is a cross-sectional view along the axial direction of the insertion body 2.

As is shown in FIG. 2, the treatment tool 1 is provided with the insertion body 2, an operating section 8, and a stylet 27.

As is shown in FIG. 3, the insertion body 2 is provided with a cylindrical needle tube 3 (treatment component) having a distal end and a proximal end, and a cylindrical sheath 7 inside which the needle tube 3 is inserted.

The material preferably used to form the needle tube 3 is a flexible material, and has sufficient resilience so that it easily returns to a rectilinear state even after being bent by an external force. For example, an alloy material such as a stainless steel alloy or a nickel-titanium alloy can be employed as the material of the needle tube 3.

FIG. 4A is an enlarged plan view showing a distal end portion of the needle tube 3, and FIG. 4B is an enlarged bottom view of the same distal end portion. As is shown in FIG. 4A and FIG. 4B, the needle tube 3 has a first aperture 31 that is provided at the distal end thereof, and a second aperture 32 that is provided closer to the proximal end side than the first aperture 31. The first aperture 31 is formed by cutting off the distal end of the needle tube on an angle relative to its own axis, and is formed with sufficient sharpness to enable it to puncture biological tissue. The specific shape of the first aperture 31 may be suitably selected from various known shapes after considering the tissue and the like that is to be punctured.

Figure 5A:
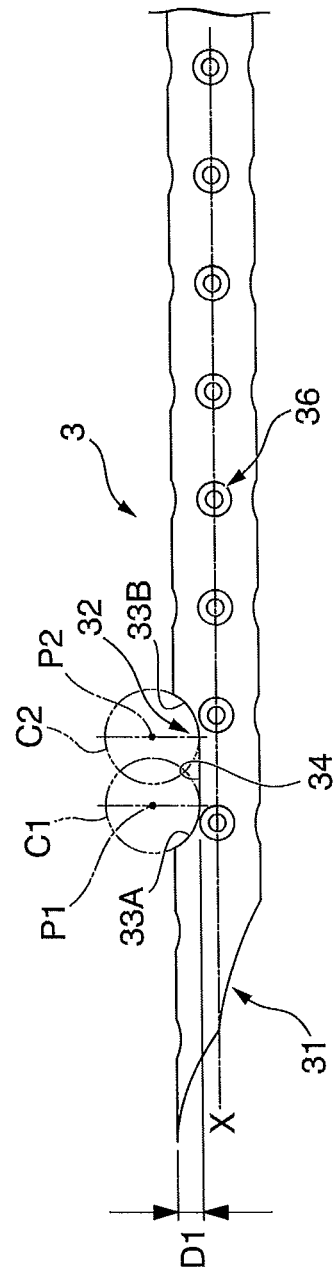
FIG. 5A is an enlarged left-side view of the distal end portion of the needle tube.
Figure 5B:
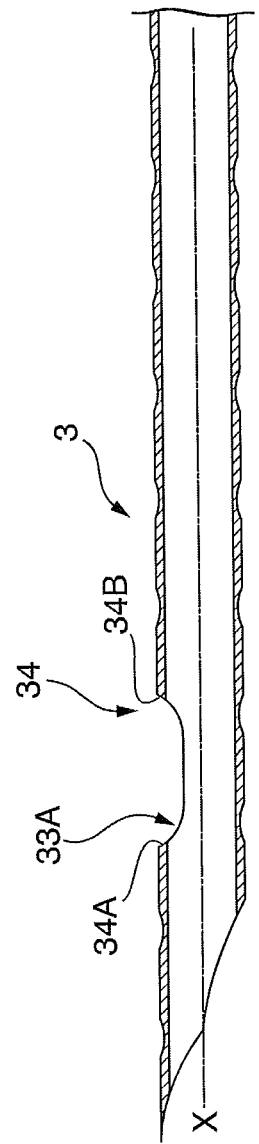
FIG. 5B is a cross-sectional view taken along a line a-a in FIG. 4A.

FIG. 5A is a left-side view of the distal end portion of the needle tube 3, FIG. 5B is a cross-sectional view taken along a line a-a shown in FIG. 4A (namely, in the depth direction of the second aperture 32). As is shown in FIG. 4A, the second aperture 32 is formed so as to communicate with the lumen by removing a portion of the outer circumferential surface of the needle tube 3. An end surface of the second aperture 32 is formed so as to have the surface area thereof which can be seen in the planar view of the second aperture, and as is shown in FIG. 4A and FIG. 5A, the end surface of the second aperture 32 is provided with circular arc portions 33 that are formed in a circular arc shape when the second aperture 32 is seen from a side view, and with rectilinear portions 34 that connect the circular arc portions 33 together.

The circular arc portion 33 has a first circular arc portion 33A, which is on the distal end side, and a second circular arc portion 33B, which is on the proximal end side. The first circular arc portion 33A and the second circular arc portion 33B are set such that, when the second aperture 32 is seen from the side view, they form a portion of the circular arcs of the circles C1 and C2 that are centered respectively on the points P1 and P2. As a result, as is shown in FIG. 5B, the proximal end side of the first circular arc portion 33A and the distal end side of the second circular arc portion 33B form edges 34A and 34B that are at an acute angle relative to the axis X of the needle tube 3, and this allows the first circular arc portion 33A and the second circular arc portion 33B to function as blade portions for cutting tissue.

Parameters that affect the functioning of the blade portions such as the surface areas in the planar view of the first circular arc portion 33A and the second circular arc portion 33B, and the angle thereof relative to the axis X can be set to various values by adjusting the radii of the aforementioned circles C1 and C2 that determine the radius of curvature of the circular arc shapes, and by adjusting the positions of the points P1 and P2 that form the centers of the circles C1 and C2. The further the positions of the points P1 and P2 from the axis of the needle tube is, or alternatively, the larger the radii of the circles C1 and C2 is, the greater the surface area in the planar view becomes, and the narrower the angle relative to the axis X becomes, so that the sharpness of the edge increases. However, care must be taken as if the thickness of the blade portion is made too thin, it may lack the necessary strength to function as a blade portion, and the ability of the blade portion to cut tissue may deteriorate.

In the present embodiment, for example, when the outer diameter of the needle tube 3 is 0.7 mm, the distance between the points P1 and P2 and the axis X is set to 0.7 mm, and the radii of the circles C1 and C2 is set to 0.5 mm. Moreover, by setting the depth D1 in the planar view of the second aperture 32 to half of the outer diameter of the needle tube 3 or less (namely, such that it does not reach as far as the axis X), the strength of the needle tube is maintained.

The second aperture 32 opens on the opposite side from the first aperture 31 so that the axis X is sandwiched between them, and the phase thereof is offset 180° in the circumferential direction of the needle tube 3. Moreover, the second aperture 32 is formed away from the first aperture 31 with a predetermined distance so as to not overlap with the first aperture 31 in the axial direction of the needle tube 3. As is described below, from the standpoint of facilitating the collection of tissue, the second aperture 32 is preferably formed within a range of 2 mm or more and 80 mm or less from the distal end of the needle tube.

Moreover, in order to improve a reflection performance to the ultrasonic wave, a plurality of dimples 36 are formed on the outer circumferential surface of the needle tube 3.

As is shown in FIG. 2, the sheath 7 is formed by a flexible tubular component made from metal coils or resin or the like, and extends from the distal end of the operating section 8. Examples of resins that can be used for the material of the sheath 7 include polyether ether ketone (PEEK), fluorine series resins, olefin series resins, urethane series resins, and nylon series (polyamide series) resins and the like. Note that a proximal end of the sheath 7 is fixed to an operating body 9 (described below) inside the operating section 8.

The operating section 8 is provided with the operating body 9, a sheath adjuster 18 that is provided at the distal end side of the operating body 9, and a needle slider 23 that is provided at the proximal end side of the operating body 9.

The operating body 9 is provided with a grip 10 that is held by a user when they are using the treatment tool 1, a slide rail 13 that extends from the grip 10 towards the proximal end side of the operating section 8, and a slider stopper 14 that is provided on the slide rail 13.

Figure 6:
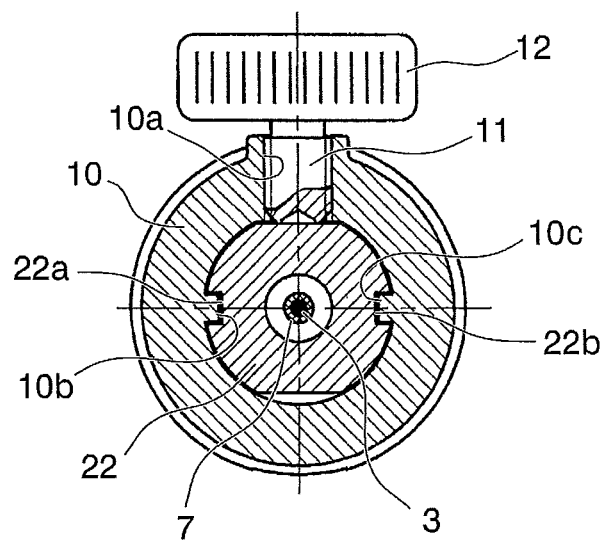
FIG. 6 is a cross-sectional view taken along a line A-A in FIG. 2.

FIG. 6 is a cross-sectional view taken along a line A-A in FIG. 2.

As is shown in FIG. 2 and FIG. 6, the grip 10 is formed in a substantially circular cylinder shape, and a screw hole 10a that penetrates the grip 10 in the thickness direction thereof, and that is used to attach a screw 11 that fixes the sheath adjuster 18 in position is formed in an outer surface of the grip 10. Moreover, a pair of projections 10b and 10c that fit inside a groove in a slide rail 22 (described below) of the sheath adjuster 18 are formed inside the grip 10.

A distal end of the screw 11 is able to be attached to the outer surface of the slide rail 22 (described below), and an enlarged diameter portion 12 that has a larger diameter than the shaft thereof is provided on the head portion of the screw 11. Furthermore, a plurality of grooves is formed in the outer circumference of the large diameter portion 12. As a result, the screw 11 can be easily turned by hand.

Figure 7:
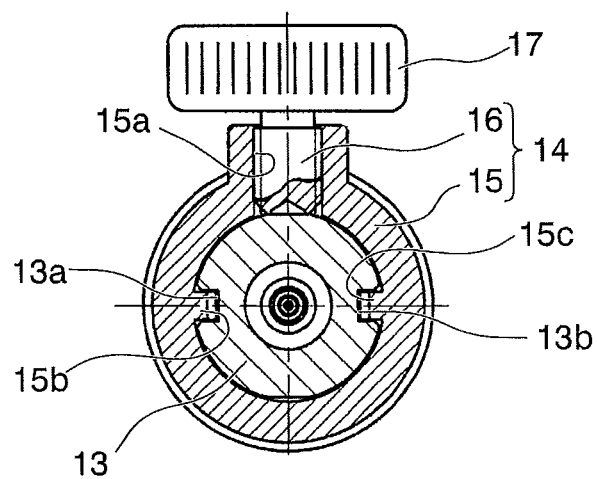
FIG. 7 is a cross-sectional view taken along a line B-B in FIG. 2.

FIG. 7 is a cross-sectional view taken along a line B-B in FIG. 2.

As is shown in FIG. 2 and FIG. 7, the slide rail 13 is a substantially circular cylinder-shaped component that is used to move the needle slider 23 forwards in backwards in the direction of a center axis of the needle slider 23, and grooves 13a and 13b that extend in parallel with this center axis are formed in an outer surface thereof. The grooves 13a and 13b are each placed at opposite directions in the radial direction of the slide rail 13. Moreover, the portion of the outer circumferential surface of the slide rail 13 that comes into contact with the distal end of the screw 16 (described below) is formed flatly.

The slider stopper 14 has a collar component 15 into which the slide rail 13 is inserted and in which a screw hole 15a that penetrates the collar component 15 in the thickness direction thereof is formed, and a screw 16 that is screwed into the screw hole 15a in the collar component 15.

The collar component 15 has a slightly larger internal diameter than the diameter of the slide rail 13, and is attached to the slide rail 13 such that it is able to move forwards and backwards in the direction of the center axis of the slide rail 13. Projections 15b and 15c that are formed on the collar component 15 and are inserted into the grooves 13a and 13b, and this prevents the collar component 15 from turning in the circumferential direction of the slide rail 13.

The distal end of the screw 16 is able to be came into contact with the outer circumferential surface of the slide rail 13, and by screwing the screw 16 into the screw hole 15a in the collar component 15, the collar component 15 can be fixed to the slide rail 13. Moreover, a large diameter portion 17 that is formed with an enlarged diameter is provided on the proximal end of the screw 16, and a plurality of grooves are formed in the outer circumference of the large diameter portion 17. As a result, the screw 16 can be easily turned by hand.

Figure 8:
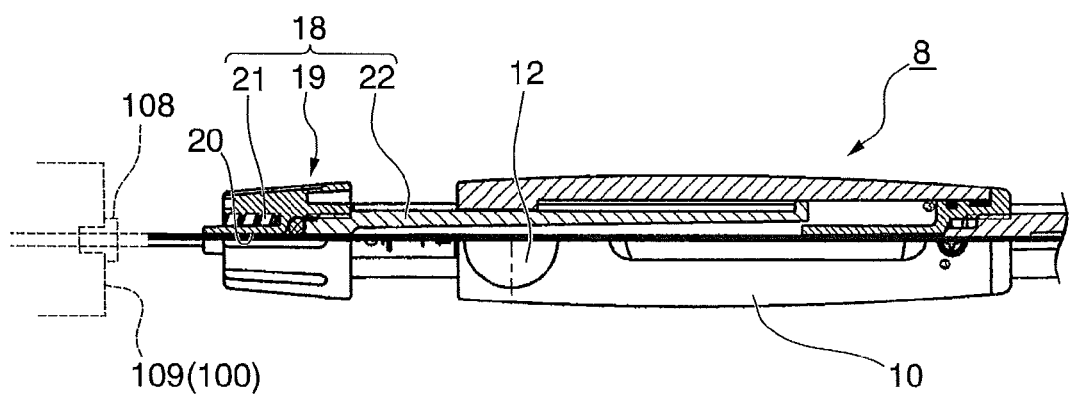
FIG. 8 is a semi-cross-sectional view showing the vicinity of a sheath adjuster of an operating portion of the treatment tool.

FIG. 8 is a semi-cross-sectional view showing the vicinity of the sheath adjuster 18 of the operating section 8.

As is shown in FIG. 1, the sheath adjuster 18 is used to adjust the amount that the sheath 7 protrudes from a distal end of the channel 107 in the ultrasonic endoscope 100. As is shown in FIG. 8, the sheath adjuster 18 is provided with a fixing screw portion 19 that is fixed to the proximal end connector 108 of the ultrasonic endoscope 100, and with the slide rail 22 that is fixed to the fixing screw portion 19 and is inserted inside the grip 10.

A through hole 20 through which the sheath 7 is inserted, and a threaded groove 21 that is used for attaching the fixing screw portion 19 to the proximal end connector 108 are formed in the fixing screw portion 19. Moreover, corrugations that function as antiskid when the fixing screw portion 19 is being connected to the proximal end connector 108, or when the fixing screw portion 19 is being disconnected from the proximal end connector 108 are formed on the outer circumferential surface of the fixing screw portion 19.

As is shown in FIG. 6 and FIG. 8, the slide rail 22 is a circular cylinder-shaped component in which are formed a pair of grooves that extend in parallel with the center axis. The sheath 7 and the needle tube 3 are inserted through the interior of the slide rail 22. A distal end of the slide rail 22 is fixed to the fixing screw portion 19, and the slide rail 22 is inserted inside the grip 10. A pair of grooves 22a and 22b that face each other in the radial direction and are elongated in the axial direction are formed in the outer circumferential surface of the slide rail 22. The projections 10b and 10c that are formed on the grip 10 fit respectively inside the grooves 22a and 22b.

Inside the grip 10, the distal end of the screw 11 that is screwed into the screw hole 10a of the grip 10 is able to come into contact with the outer surface of the slide rail 22. Consequently, when the screw 11 is screwed into the grip 10, the slide rail 22 and the grip 10 are locked together as a result of the distal end of the screw 11 being pushed up against the outer surface of the slide rail 22. When this screw 11 is loosened, the slide rail 22 of the sheath adjuster 18 and the grip 10 are able to move relatively in the longitudinal direction of the grooves.

Figure 9:
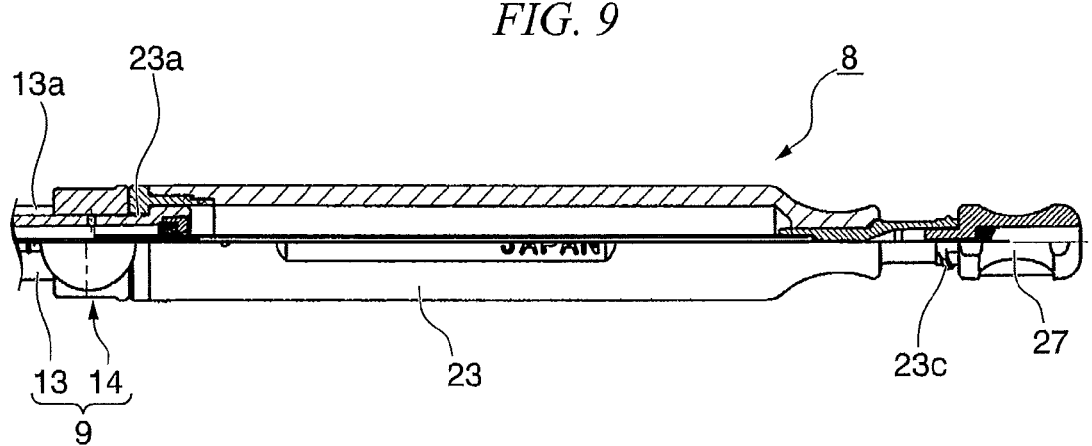
FIG. 9 is a semi-cross-sectional view showing an enlargement of a needle slider of the operating portion.
Figure 10:
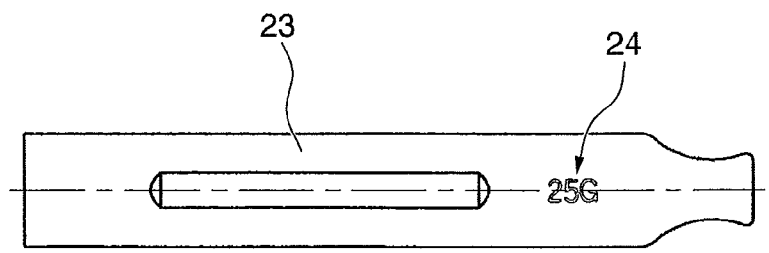
FIG. 10 is a view looking in the direction of an arrow C in FIG. 2 showing an enlargement of the needle slider.

FIG. 9 is a semi-cross-sectional view showing an enlargement of the needle slider 23 of the operating section 8. FIG. 10 is a view looking in the direction of an arrow C in FIG. 2 showing an enlargement of the needle slider 23 of the operating section 8.

As is shown in FIG. 9, the needle slider 23 is a cylindrical component, and the slide rail 13 of the operating body 9 is inserted inside this needle slider 23. A pair of projections 23a (one of the two projections 23a is omitted from the drawing) that fit inside the grooves 13a and 13b of the slide rail 13 are formed on the needle slider 23. A distal end of the needle slider 23 is able to come into contact with a proximal end of the slider stopper 14. A knob 28 and a screw thread 23c that is used for screwing on a syringe 120 are formed on a proximal end of the needle slider 23.

An outer surface of the needle slider 23 has a columnar-shaped outer surface that enables it to be gripped by the user who is using the treatment tool 1. Furthermore, as is shown in FIG. 10, a gauge number display portion 24 where gauge numbers that show the diameter of the needle tube 3 are displayed by means of engraving or the like is formed on the outer surface of the needle slider 23.

Although not shown in detail, a proximal end of the needle tube 3 is fixed to an interior portion of the needle slider 23. The stylet 27 (described below) can be inserted via the proximal end of the needle tube 3 that is fixed to the needle slider 23. By moving the needle slider 23 in the direction of the center axis thereof along the grooves 13a and 13b in the slide rail 13 (see FIG. 7), the needle tube 3 can be made to protrude from the sheath 7 or can be retracted into the sheath 7.

Moreover, the needle slider 23 and the slide rail 13 are joined together such that they do not become disconnected from each other when the needle slider 23 is moved towards the proximal end side of the slide rail 13. When the needle slider 23 has been moved to a maximum movable position of the proximal end side of the slide rail 13, a position between the distal end of the needle tube 3 that is fixed to the needle slider 23 and the sheath 7 such that the distal end of the needle tube 3 is drawn inside the distal end of the sheath 7, and is covered by the sheath 7.

FIG. 11 is a side view of the stylet 27. FIG. 12 is a cross-sectional view taken along a line D-D in FIG. 11.

As is shown in FIG. 11 and FIG. 12, the stylet 27 is formed from a metal wire material having a diameter size that enables it to be inserted inside the needle tube 3 and moved backwards and forwards freely. A distal end of the stylet 27 is extremely sharp, and the knob 28, which is formed from resin or the like, is provided on a proximal end of the stylet 27. Note that as is shown in FIG. 11B, the distal end of the stylet 270 may also be formed in a substantially hemispherical configuration.

A gauge number display portion 29 where the gauge number of the needle tube 3 in which the stylet 27 can be properly inserted is displayed by means of engraving or the like is formed on the knob 28 that is provided on the proximal end of the stylet 27. Namely, provided that the stylet 27 has a numerical value displayed on the knob 28 that is the same as the gauge number displayed on the gauge number display portion 24 provided on the needle slider 23, then that stylet 27 can be properly inserted inside the needle tube 3 and then used. By doing this, it is possible to avoid the mistakes in choosing a needle tube 3 and a stylet 27 that may occur when a plurality of treatment tools 1, that these needle tubes 3 and stylets 27 are differing diameters, are used during one operation.

As is shown in FIG. 12, a threaded groove 28a with which the screw thread 23c (see FIG. 9) is able to engage is formed in the knob 28. The threaded groove 28a fits the screw thread 23c that is formed on the proximal end of the needle slider 23. By setting the screw thread 23c of the needle slider 23 and the threaded groove 28a of the knob 28 and screwing the knob 28, the stylet 27 can be fixed to the needle slider 23. At this time, the distal end of the stylet 27 is set in a position where it protrudes slightly from the distal end of the needle tube 3 (see FIG. 3).

A method of using the treatment tool 1 having the above-described structure and operations that are performed when this treatment tool 1 is used will now be described. FIG. 13 through FIG. 18B are operational explanatory views illustrating operations when using the treatment tool 1.

Figure 13:
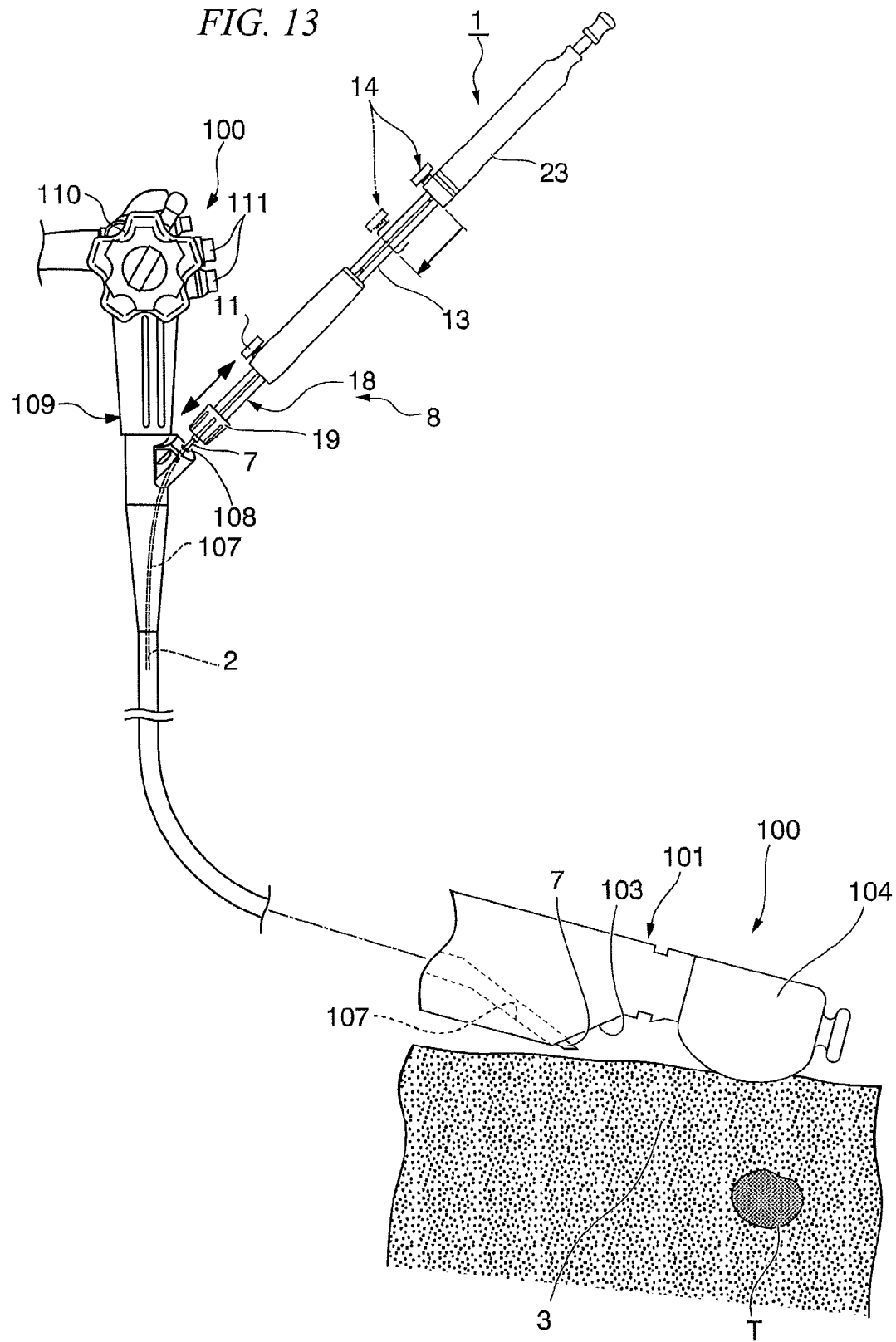
FIG. 13 is a view used to explain an operation when this treatment tool is being used.

In the present embodiment, as is shown in FIG. 13, a biopsy treatment in which the needle tube 3 of the treatment tool 1 is inserted into lesion tissue that is located in a deep portion of the tissue in a body, and lesioned cells and the like are collected through the interior of the needle tube 3 is described as an example.

As is shown in FIG. 13, a user inserts the insertion portion 101 of the ultrasonic endoscope 100 into a body, and then, optically observes the area where treatment is to be performed by using the optical imaging mechanism 103. In addition, the user observes the deep portion of the area where the treatment is to be performed by using the ultrasonic scanning mechanism 104.

Next, based on the results of the observations made using the optical imaging mechanism 103 and the ultrasonic scanning mechanism 104, the user determines the area where the biopsy is to be performed.

Next, the user inserts the distal end side of the insertion body 2 of the treatment tool 1 inside the channel 107 via the proximal end connector 108 that is provided in the operating section 109 of the ultrasonic endoscope 100. Furthermore, the user fixes the fixing screw portion 19 that is provided on the operating section 8 of the treatment tool 1 to the proximal end connector 108. By doing this, the treatment tool 1 is fixed to the ultrasonic endoscope 100.

Next, the user loosens the screw 11 provided on the grip 10 and, while observing the sheath 7 and the body interior via the optical imaging mechanism 103, uses the sheath adjuster 18 to adjust the amount that the sheath 7 protrudes from the distal end of the insertion portion 101 of the ultrasonic endoscope 100 to a suitable amount.

Next, based on the results of the observation made by the ultrasonic scanning mechanism 104, the user moves the slider stopper 14 in accordance with the position of the subject tissue T that is to be biopsied, and then fixes it to the slide rail 13. By doing this, the maximum length that the needle tube 3 is able to protrude from the sheath 7 is limited to the length that the needle slider 23 is able to protrude until it comes into contact with the slider stopper 14.

Figure 14:
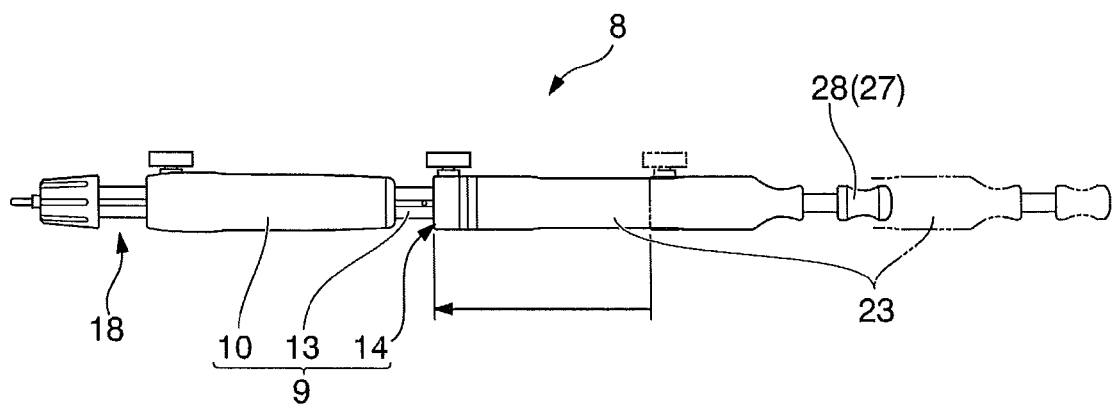
FIG. 14 is a view used to explain an operation when this treatment tool is being used.
Figure 15:
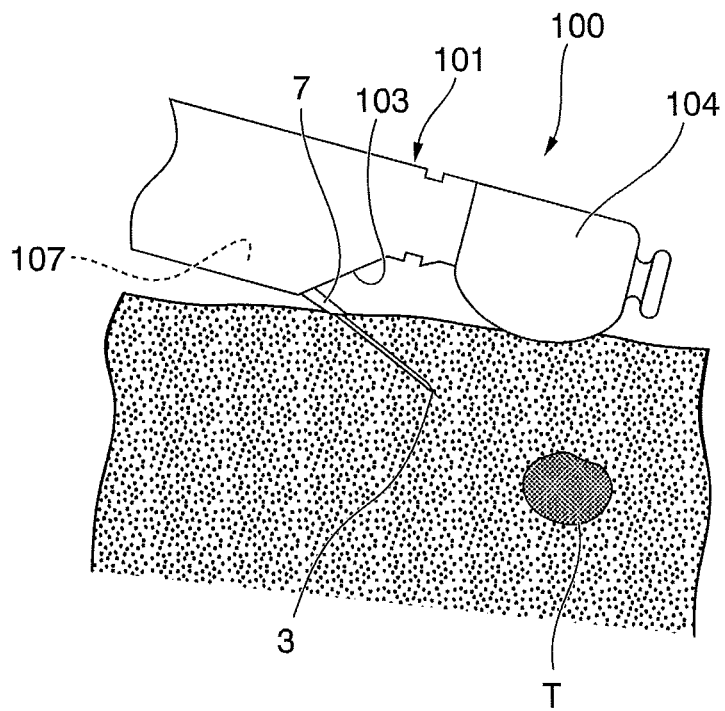
FIG. 15 is a view used to explain an operation when this treatment tool is being used.
Figure 16:
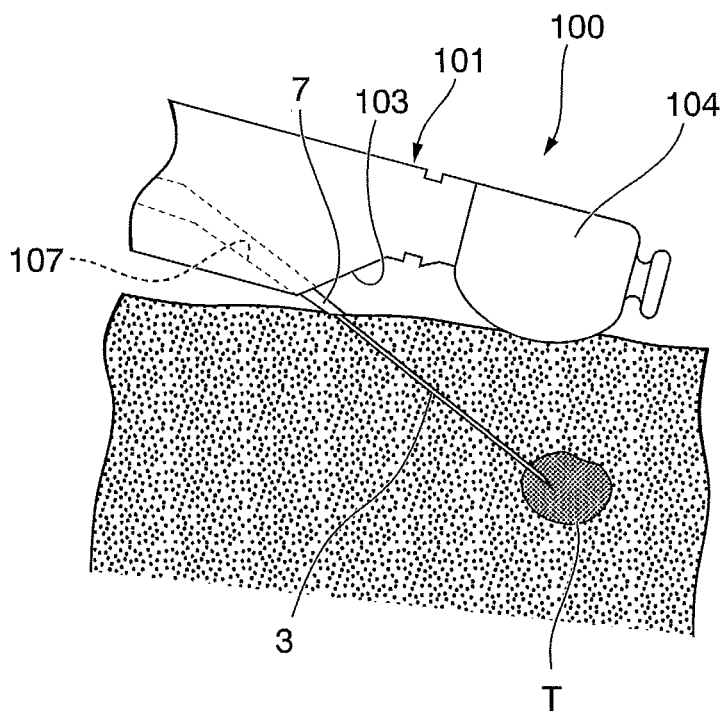
FIG. 16 is a view used to explain an operation when this treatment tool is being used.

Next, as is shown in FIG. 14, the user pushes the needle slider 23 towards the distal end side of the operating section 8. As a result of this, as is shown in FIG. 15, the needle tube 3 protrudes from the sheath 7. Furthermore, as is shown in FIG. 16, the distal end of the needle tube 3 punctures the tissue, and is pushed further into the subject tissue T that is to be biopsied.

At this time, the needle tube 3 that is exposed to the outside at the surface of the tissue can be observed by the optical imaging mechanism 103, and the portion on the distal end side of the needle tube 3 that has been inserted into the tissue can be observed by the ultrasonic scanning mechanism 104. Since the second aperture 32 is formed such that, when the second aperture 32 is looked at in its own planar view, the aperture end surface thereof that is formed by the circular arc portions 33 and the rectilinear portions 34 has a surface area, ultrasonic waves can be reflected excellently and provides excellent observations.

The user is able to observe ultrasonic images that are based on the ultrasonic waves received by the ultrasonic scanning mechanism 104 by the ultrasonic observation unit 115 shown in FIG. 1. While referring to the images of the needle tube 3 that are displayed in great detail on the ultrasonic observation unit 115, the user brings the distal end of the needle tube 3 to the subject tissue T that is to be biopsied. Note that at the stage when the distal end of the needle tube 3 has reached the subject tissue T that is to be biopsied, because the stylets 27 is inserted in the needle tube 3, tissue does not enter inside the needle tube 3.

Figure 17:
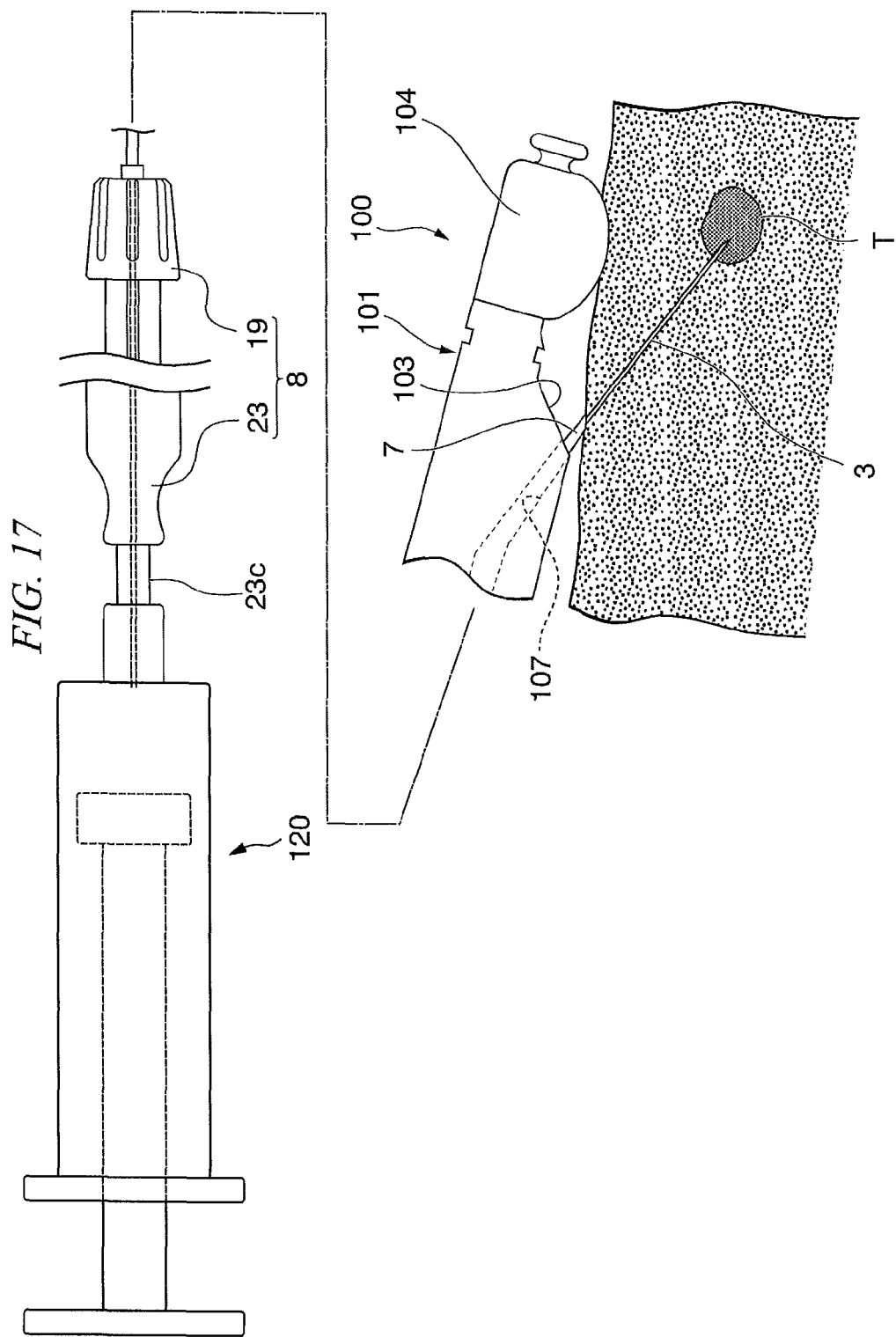
FIG. 17 is a view showing a process of a treatment procedure using this treatment tool.

Next, the user turns the knob 28 of the stylet 27 shown in FIG. 2 and removes the knob 28 from the needle slider 23, and extracts the stylet 27 from the insertion body 2 and the operating section 8. By doing this, as is shown in FIG. 17, a through hole is formed that extends from the distal end of the needle tube 3 as far as the proximal end of the needle slider 23. The user then fixes a suitable syringe 120 to the screw 23c whose distal end is able to be engaged with the screw thread 23c formed on the proximal end of the needle slider 23. The interior of the needle tube 3 is then suctioned by the syringe 120, so that the cells and the like of the subject tissue T that is to be biopsied are suctioned inside the syringe 120 from the distal end of the needle tube 3.

In the needle tube 3 that is piercing the subject tissue T, because a portion of the subject tissue T has intruded inside the second aperture 32, the subject tissue is also suctioned from the second aperture 32, so that the tissue can be collected extremely efficiently.

Once the required amount of cells and the like has been suctioned into the syringe 120, the needle slider 23 is pulled fully back to the proximal end side of the operating section 8, and the distal end of the needle tube 3 is housed inside the sheath 7. As a result, the needle tube 3 is withdrawn from the tissue. Once the needle tube 3 has been withdrawn from the tissue, the fixing screw portion 19 is removed from the proximal end connector 108 of the operating portion 109 of the ultrasonic endoscope 100, and the treatment tool 1 is removed from the channel 107. This ends the processing sequence.

Figure 18A:
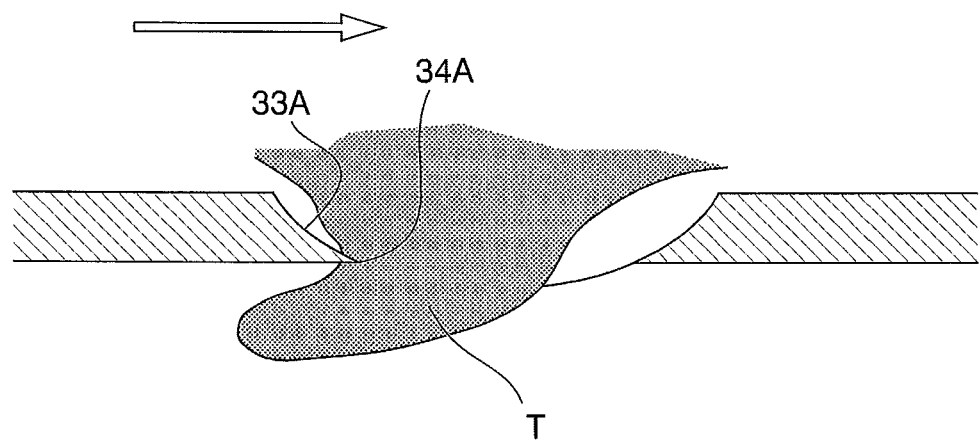
FIG. 18A is a view showing a process of a treatment procedure using this treatment tool.
Figure 18B:
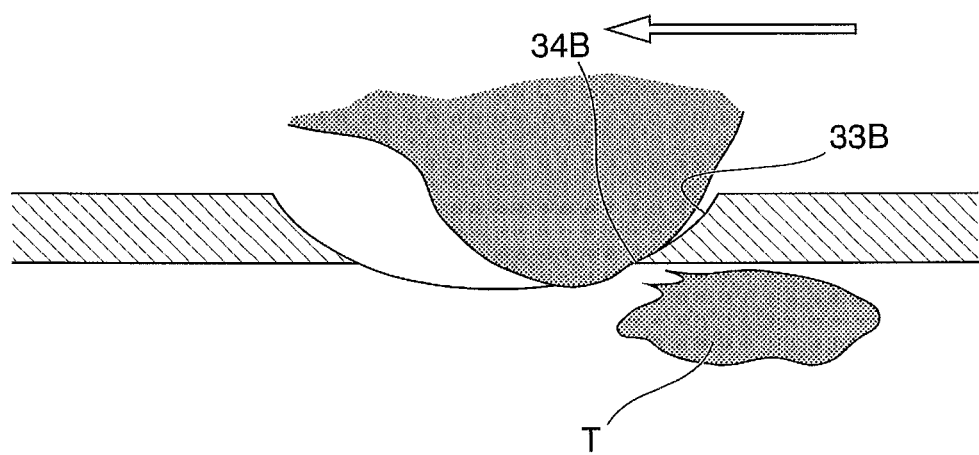
FIG. 18B is a view showing a process of a treatment procedure using this treatment tool.

In cases such as when the amount of collected tissue is insufficient, if the user moves the needle tube 3 forwards and backwards in the axial direction, then when it is being moved backwards, as is shown in FIG. 18A, the subject tissue is cut into by the edge 34A of the first circular arc portion 33A, while when it is being moved forwards, as is shown in FIG. 18B, the subject tissue is cut into by the edge 34B of the second circular arc portion 33B. Accordingly, the user is able to cut off a portion of the subject tissue in the second aperture 32, and thereby improve the tissue collectability by moving the needle tube 3 forwards and backwards several times in the axial direction.

Conventionally, by forming a hole in the outer circumferential surface of the puncture needle, attempts have been made to increase the amount of tissue collection, and to make it possible to collect tissue even when the distal end aperture has become blocked and the like. However, these attempts have amounted to nothing more than forming a hole in the outer circumferential surface of the puncture needle, and the internal walls of such holes are largely orthogonal to the axis of the needle.

Because internal walls that are orthogonal to the axis of the needle reflect substantially no ultrasonic waves, the problem has existed that it has been difficult to observe a location where a hole is formed in the outer circumferential surface using ultrasonic waves.

In the treatment tool 1 of the present embodiment, because the circular arc portions 33 and the rectilinear portions 34 of the second aperture 32 are formed such that they have a sufficient surface area when the second aperture is seen in planar view, they excellently reflect ultrasonic waves, and it is possible to make proper observations and verify the location even when the area is being observed ultrasonically.

Moreover, since the second aperture 32, which has the circular arc portions 33 formed on both sides thereof in the axial direction, is provided separately from the first aperture 31, which is formed at the distal end of the needle tube 3, the circular arc portions 33 function as blade portions, and subject tissue can be cut off and collected by moving the needle tube 3 forwards and backwards.

Furthermore, since the phases in the circumferential direction of the needle tube 3 of the first aperture 31 and the second aperture 32 are offset, they come into contact with different surfaces of the subject tissue during the forwards and backwards movement. Accordingly, even if a surface touched by the first aperture 31 is difficult to cut off because of, for example, fibrosis or the like, the second aperture 32 comes into contact with a different surface so that the probability that tissue collection will be possible is greatly improved.

While a preferred embodiment of the invention has been described and illustrated above, it should be understood that this are exemplary of the invention and is not to be considered as limiting. Additions, omissions, substitutions, and other modifications can be made without departing from the spirit or scope of the present invention.

For example, regarding the shape of the second aperture, it is not essential that both ends in the axial direction be formed as circular arcs, provided that they are curves that form the above described edges when looked at in the planar view. Moreover, if both ends are formed as circular arcs, then instead of forming those using different circles on the distal end side and the proximal end side, as is described above, the distal end side and the proximal end side may be formed as portions of the circular arc of the same circle. In this case, since the first circular arc portion and the second circular arc portions are continuous with each other, the rectilinear portions are no longer required in the second aperture.

Figure 19A:
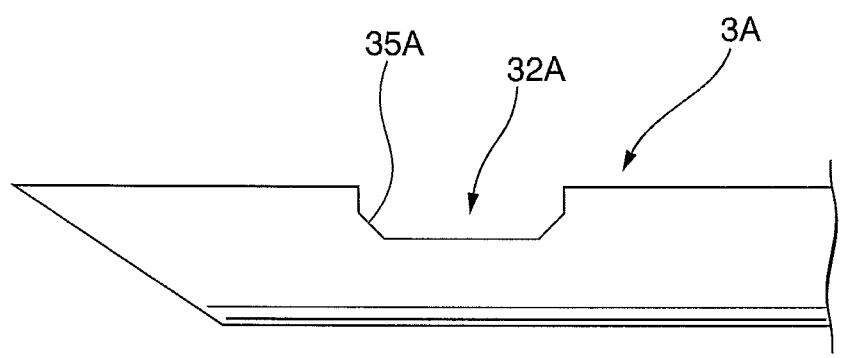
FIG. 19A is a view showing a distal end portion of a needle tube in a modified example of the treatment tool.
Figure 19B:
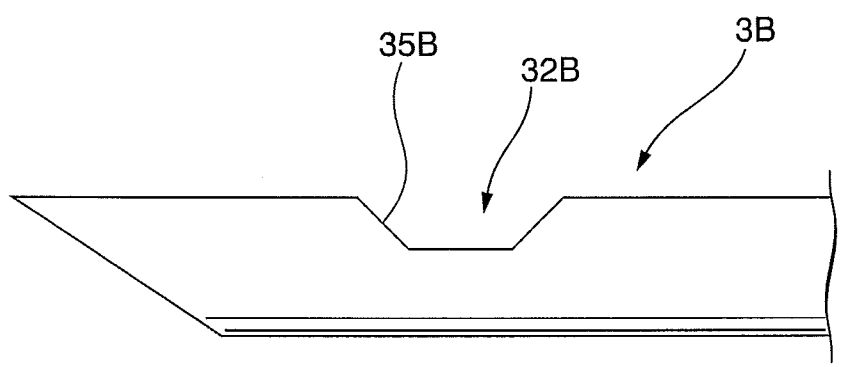
FIG. 19B is a view showing a distal end portion of a needle tube in a modified example of the treatment tool.

Furthermore, although the above described effects are limiting, as in the case of a needle tube 3A and 3B of the modified examples shown in FIG. 19A and FIG. 19B, second apertures 32A and 32B may be formed so as to consist of only straight lines areas when looked at in side view. In this case, the shape of the second aperture may be set such that inclined surfaces 35A and 35B that are inclined at an acute angle relative to the axis X are formed in at least a portion of both end portions in the axial direction.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as limited by the foregoing description and is only limited by the scope of the appended claims.

What is claimed is:

1. A treatment tool for biopsy comprising
a needle tube which is formed with a tubular space and a sharp distal end that is capable of piercing tissue, the needle tube having a first aperture, a second aperture, and at least a first dimple, wherein
the first aperture is provided in the distal end of the needle tube and communicates with the tubular space,
the second aperture is provided, in order to collect tissue from an area punctured by the needle tube, in a side surface of the needle tube at more proximal end side than the first aperture, and communicates with the tubular space in the needle tube,
an end surface of the second aperture comprises both a distal end circular arc portion which is formed in circular arc shape on the distal end side and a proximal end circular arc portion which is formed in circular arc shape on the proximal end side in an axial direction of the needle tube,
in a cross-section taken in a depth direction of the second aperture so as to include an axis of the needle tube, the distal end circular arc portion comprises a distal end side inclined surface that is inclined so as to be positioned gradually outwards of a radial direction of the needle tube towards the distal end side of the second aperture, and the proximal end circular arc portion comprises a proximal end inclined surface that is inclined so as to be positioned gradually outwards of the radial direction of the needle tube towards the proximal end side of the second aperture,
blade portions that are used to cut off tissue when the needle tube is moved backwards and forwards in the axial direction of the needle tube are formed on end portions of the distal end side inclined surface and the proximal end inclined surface that are on the second aperture side,
the second aperture is formed at a different phase position in comparison to a proximal end of the first aperture in the circumferential direction of the needle tube without overlapping the first aperture in the axial direction of the needle tube, and
the at least first dimple is formed at a phase position including the second aperture in the circumferential direction of the needle tube and at a position between a distal end of the needle tube and the second aperture.

2. The treatment tool for biopsy according to claim 1, wherein in the cross-section taken in the depth direction of the second aperture, the distal end side inclined surface and the proximal end inclined surface are formed such that portions of circular arcs of circles whose centers are predetermined points located outside the needle tube in the radial direction thereof.

3. The treatment tool for biopsy according to claim 1, wherein the end surface of the second aperture is provided with rectilinear portions that connect gently to a proximal end portion of the distal end circular arc portion and to a distal end portion of the proximal end circular arc portion, and that extend in the axial direction of the needle tube, and
the rectilinear portions include a non-inclined surface formed in parallel with the axial direction of the needle tube and facing the second aperture.

4. The treatment tool for biopsy according to claim 3, wherein
the at least first dimple includes a second dimple formed along the axial direction of the needle tube at the phase position including the second aperture in the circumferential direction of the needle tube, and
the second aperture is positioned between the first dimple and the second dimple.

5. The treatment tool for biopsy according to claim 4, wherein
the needle tube includes an outer circumferential surface of the needle tube,
the at least first dimple includes a third dimple formed on the outer circumferential surface at an opposite side of the second aperture sandwiching the axis of the needle tube.

6. The treatment tool for biopsy according to claim 1, wherein the second aperture is formed on the outer circumferential surface at an opposite side from the proximal end of the first aperture sandwiching the axis of the needle tube.

* * * * *